United States Patent [19]

Bredemeier

[11] Patent Number: 5,000,051

[45] Date of Patent: Mar. 19, 1991

[54] LYSIMETER PROBE WHICH MAY BE INSERTED INTO THE GROUND

[76] Inventor: Michael Bredemeier, Beyerstrasse 40, 3400 Göttingen, Fed. Rep. of Germany

[21] Appl. No.: 396,943

[22] Filed: Aug. 21, 1989

[30] Foreign Application Priority Data

Aug. 22, 1988 [DE] Fed. Rep. of Germany ....... 3828468

[51] Int. Cl.⁵ .................... G01N 1/10; G01N 33/24
[52] U.S. Cl. ................................. 73/863.23; 73/73; 73/864.74
[58] Field of Search ........... 73/863.23, 863.24, 863.25, 73/73, 74, 75, 76, 77, 864.74, 864.34, 864.35

[56] References Cited

U.S. PATENT DOCUMENTS

| | | | |
|---|---|---|---|
| 3,374,664 | 3/1968 | Lefelhocz et al. | 73/73 |
| 3,830,106 | 8/1974 | Gardiner et al. | 73/863.23 |
| 3,835,710 | 9/1974 | Pogorski | 73/864.74 |
| 4,261,203 | 4/1981 | Snyder | 73/864.74 |
| 4,332,172 | 6/1982 | Torstensson | 73/73 X |
| 4,408,481 | 10/1983 | Sidey | 73/73 |
| 4,692,287 | 9/1987 | Timmons | 73/863.23 X |
| 4,804,050 | 2/1989 | Kerfoot | 73/864.74 X |
| 4,923,333 | 5/1990 | Timmons | 73/863.23 X |

FOREIGN PATENT DOCUMENTS

| | | | |
|---|---|---|---|
| 62022 | 10/1982 | European Pat. Off. | 73/863.23 |
| 2747621 | 4/1979 | Fed. Rep. of Germany | 73/73 |
| 472230 | 9/1954 | Italy | 73/73 |
| 400618 | 4/1966 | Switzerland | 73/73 |
| 699092 | 11/1979 | U.S.S.R. | 73/73 |
| 2137760 | 10/1984 | United Kingdom | 73/73 |

*Primary Examiner*—Tom Noland
*Attorney, Agent, or Firm*—Thomas & Kerr

[57] ABSTRACT

A lysimeter probe which may be inserted into the ground is provided with a tubular basic body (1) and a tubular body (4), the latter of which is made of a porous material. It has a connecting sleeve (10) for the application of a negative pressure to the interior space (5) of the tubular basic body (1) and the porous tubular body (4). The basic body (1) is implemented in two pieces and includes on both parts (2, 3) detachable means of connection (14, 15) between which the porous tubular body (4), which is implemented in the way of a pipe-section, is arranged between the two parts (2, 3) of the basic body (1), which are turned towards each other, in a way it may be clamped relieved from pressure.

9 Claims, 1 Drawing Sheet

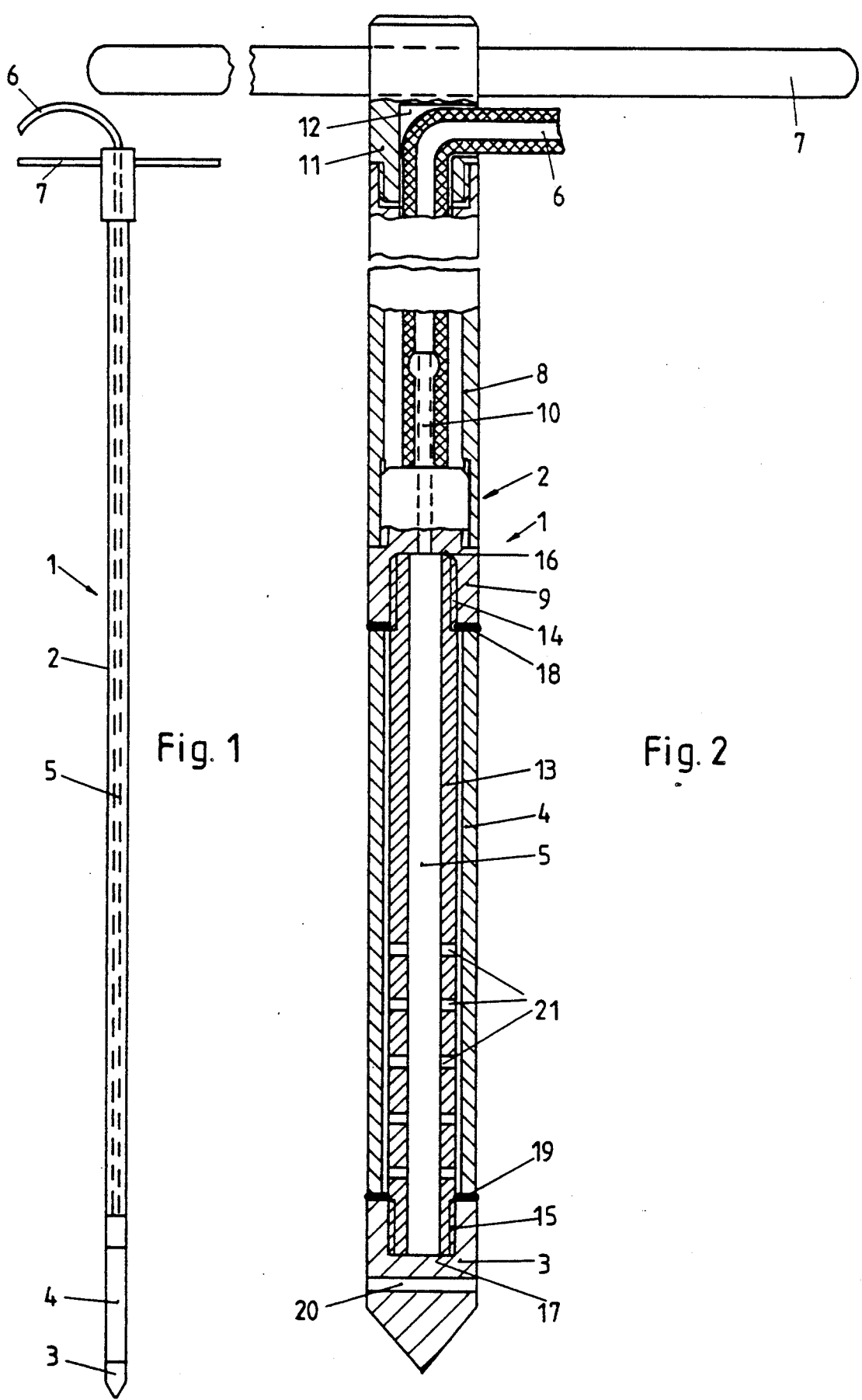

LYSIMETER PROBE WHICH MAY BE INSERTED INTO THE GROUND

FIELD OF THE INVENTION

The invention relates to a lysimeter probe which may be inserted into the ground. A lysimeter probe is a tubular body which is inserted into the ground in order to get, and examine, samples of soil solutions in the broadest sense of the word e.g. infiltration water in the unsaturated zone, ground water, banked-up water or the like. Such geo-ecologically oriented examinations are carried out particularly in the field of agro-pedology, geo-botanics, geochemistry, hydrology, etc.

BACKGROUND OF THE INVENTION

The conventional lysimeter probes are provided with a tubular basic body to which a suction cup, made of porous material, e.g. of ceramics, sintered metal or the like, is affixed on the end which is turned towards the ground. The suction cup itself forms the tip of the lysimeter probe and is mostly cylindrically or conically shaped, the free end of the suction cup being conically or roundly tipped. The suction cup is fragile, whereas the basic body is mostly made of plastics. Thus, the suction cup, which is permeable to liquids and sensitive to pressure, is in danger of being destroyed upon the insertion into the ground. Also during the removal of the lysimeter prober, for instance when it is to be used again or another site, the suction cup is in danger of being destroyed. To prevent this danger it has been known to first pilot-drill with a soil auger and then to insert the lysimeter probe into this pilot-drilled hole. However, this only reduces the danger of the destruction of the porous cup, but does not completely eliminate it. Since the porous cup must have contact with the ground in order that the solution from the ground may be taken in by the lysimetric method, forces act between the ground and the suction cup. These forces are directly transferred to the basic body so that in any way suction cup and basic body are equally stressed. Taking into consideration that such a lysimeter probe has to be driven also into rather hard soils, for instance, into pebbles, it is understandable that the destruction of the suction cup is rather the rule than the exception. As a consequence of the considerable ground contact in the area of the rounded or otherwise tapered tip, the surface of the suction cup is also considerably soiled, i.e. the soil clings to the surface of the suction cup. Thus, the suction cup is no longer appropriate for measurements on other sites, not to mention that the measurement taken on a second site may be falsified as a consequence of soil from a first place of measuring clinging to the probe. Thus, it has been known either to remove the porous suction cup from the basic body or replace it with another porous suction cup.

SUMMARY OF THE INVENTION

The aim of the present invention is to further develop a lysimeter probe as the one initially described in a way it may easily and without pilot-boring be inserted into the ground, thereby to a great extent preventing the danger of destruction of the pressure-sensitive porous interface.

According to the present invention this is achieved in that the basic body has two parts and that detachable means of connection are provided on either of the two parts between which a porous body, which is implemented in pipe-section form, is arranged between the ends of the two parts of the basic body, which are turned towards each other, in a way that it is relieved from pressure and may be clamped. The new lysimeter probe moves away from the conventional way of construction and provides a basic body which is made of two parts, whereby the one part of the basic body represents the rear end and the other part of the basic body the front part of the lysimeter probe, whereby the latter part is also moved in front of the other as tip when the probe is inserted into the ground. Between these two parts of the basic body, which are connected to each other in a way that they may at any time be detached, a porous body having the form of a pipe section is clamped without being subjected to pressure. Thus, the porous body is cylindrically shaped and itself has no tip or rounded part. Its outside diameter is constant along its entire length so that it is not only easier to manufacture but also offers a more reasonable way of using it in the lysimeter probe. Any forces which may have an effect on the porous tube from the ground are always directed orthogonally to the insertion forces towards the lysimeter probe so that the porous tube is relatively little strained even if the lysimeter probe is driven into heavy soils. The substantial forces are transmitted directly between the two parts of the basic body and the porous tube is kept free from such forces. On the porous tube only those forces have an effect which were brought on it upon its assembly and which act on the tubular body also when the lysimeter probe is in no contact to the ground. These clamping forces can be minimized advantageously. By doing so the porous tube is practically kept free from such forces which upon penetration of the lysimeter probe act on the basic body. Nevertheless the porous tube is in contact with the ground, whereby the diameters of the porous tube and of the basic body are usefully matched. The porous tube, and the parts of the basic body respectively, are located on the probe so that the porous tube may easily be exchanged; thus, it can be handled quickly and without problems when it is needed for other examination sites. The pilot-boring with a soil auger has become completely superfluous. Advantageous use of the lysimeter probe is possible also in cases where, up to now, a soil extraction has been carried out.

The part of the body turned towards the porous tube and forming the tip and the other part of the basic body turned towards the porous tube have approximately the same outside diameters, whereby the outside diameter of the porous tube is smaller or equal to the outside diameter of the parts of the basic body. In this way the part of the basic body forming the tip provides an appropriate hole and the outside surface of the porous tube leans against it under the corresponding resilience of the ground without considerable forces acting on the porous tube.

The two parts of the basic body may include limit stoppers by means of which a minimal distance for the reproducible clamping of the porous tube between the parts of the basic body is determined. Thus, it is possible to put a principal limit to the clamping pressure exerted on the porous tube upon connecting the two parts and also to avoid excessive clamping pressures which would otherwise act on the porous tube.

The porous tube is preferably clamped between the two parts of the basic body by using sealing washers of an elastic material. These sealing washers have two functions. Firstly, they assure the necessary tightness, i.e. it is ensured that the solution taken from the soil is won through the cylindrical case of the porous tube only. Secondly, the sealing washers upon clamping of the porous tube are pressed together to the desired degree so that the reduced clamping forces are provided and/or determined.

The preferred detachable means of connection may have the form of a thread. However, also a bayonet socket or the like would absolutely be possible. The only important thing about this is that the two parts of the basic body may easily be detached from each other and that they can also easily be put together.

The part of the basic body forming the tip can be connected to the other part of the basic body through a transverse rod with threaded pieces, which extends through the tubular body. There are openings provided in the transverse rod, which lead to the interior space of the basic body. Thus, this connecting rod at the same time serves also the transmission of the forces from the part of the basic body which forms the tip to the other part of the basic body, under circumvention of the pressure sensitive porous tube.

On the part of the basic body which forms the tip a recess for the attachment of a twisting tool and on the other part of the basic body a transverse rod, a handle or the like may be provided. This embodiment facilitates the assembly of the basic body. Moreover, the transverse rod is meaningful to push the lysimeter probe into the ground or pull it out of the ground. In case of harder soils the lysimeter probe may also be beaten in.

In order that the invention be clearly understood two exemplary embodiments are now described with reference to the accompanying drawings, in which:

BRIEF DESCRIPTION OF THE DRAWINGS

FIG. 1 is a scaled-down first embodiment of the lysimeter probe and

FIG. 2 is a second embodiment of the lysimeter probe, shown in approximately normal size.

DETAILED DESCRIPTION

The lysimeter probe shown in FIG. 1 has a basic body 1 made of metal (preferably stainless steel), which is substantially tubular and longish in shape. The basic body 1 comprises a comparatively longer rear part 2 and a front part 3, which forms a tip, which are interconnected through detachable means of connection.

Between the two parts 2 and 3 a tubular body 4 of a porous, liquid-permeable material is clamped in a way it is relieved from pressure. In particular part 2 and the tubular body 4 embrace an interior space 5, which has the form of a channel and extends to the top of part 2 of the basic body 1. The interior space 5 is connected to a hose 6 with the help of a connecting piece (not shown) so that, by this way, the solution won from the ground which penetrates into the interior space 5 through the tubular body 4 may be drawn off. In the upper area of part 2 of the basic body 1 there is also provided a transverse rod 7 for the handling of the lysimeter probe. In particular, the lysimeter probe may easily be pulled out of the soil with the help of the transverse rod 7 after the lysimetric sampling has been terminated.

Part 2, or its connection piece 9, is connected to part 3 of the basic body 1, which forms the tip, through a connecting rod 13 in a way they may be detached from each other, whereby said connecting rod is on both ends provided with threads 14 and 15, which correspond to counter threads in the connecting piece 9 and in part 3 of the basic body 1. By means of the depth of the borings and corresponding shouldered bores the limit stoppers and 17 are formed, thus determining a minimal distance b the parts 2 and 3 of the basic body, under which one remain. It is thus ensured that, in connection with the length of the porous tube 4 and the respective matching, the porous tube 4 may be clamped in a way it is relieved from pressure. This means that the substantial forces which, upon the driving of the lysimeter probe into the soil, firstly act on part 3 of basic body, are directly transmitted via the connecting rod 13 into part 2 and that the porous tube 4 is kept free from these forces. The porous tube 4 is thus clamped, or mounted, in a way it is relieved from pressure. However, on the other hand, the porous tube 4 must also be held in a stationary position by the parts 2 and 3 of the basic body. This is preferably achieved by the attachment of sealing washers 18 and 19, which are made of an elastic material, e.g. of silicone. By the choice of the measurements between the limit stoppers 16 and 17 on the one hand and the length of the porous tube 4 and the thickness of the sealing washers 18 and 19 on the other, the measure is determined with which the porous tube 4 is held between the parts. These forces act on the porous tube 4 only as a consequence of its being clamped and are minimized by the arrangement of the limit stoppers 16 and 17. On the other hand the sealing washers 18 and 19 provide the necessary tightening on the end faces of the porous tube 4. The sealing washers 18 and 19 also serve for a stationary mounting.

Also the outside diameters of part 3 and part 2 and, respectively, in particular that of the connecting piece 9 as well as the outside diameter of the porous tube 4, are matched. The said diameters are usually equal. Only the outside diameter of the porous tube 4 may perhaps be slightly smaller than the outside diameter of the cylindrical piece of part 3 of the basic body 1. By using this measure it must, however, still be ensured that the porous tube 4 upon its insertion with the lysimeter probe gets into contact with the ground.

Part 3, which forms the tip of the lysimeter probe can preferably have a recess 20, here implemented in the form of a cross hole, in order to provide paint of leverage for forces relative to the transverse rod 7 on the other part 2, so that the detachable means of collection, namely the threads 14 and 15, or at least one of them, may easily be unscrewed when a porous tube 4 has to be put in or has to be exchanged. As a matter of fact the connecting rod 13 can also be implemented in one piece with part 3. In any case, it has openings 21 through which the solution to be won from the soil may pass from outside through the porous tube 4 finally into the interior space 5 and then to the hose 6. Usually a vacuum source or evacuated sample container, preferably a bottle, is connected to the hose 6. Further, it can be seen that the connecting piece 9 may also be implemented in one piece with the central piece 8 of part 2, a corresponding thread connection then being no longer necessary. Further possible ways of modification are not unthinkable. What is important is primarily the pressure-relieved clamping of the porous tube 4 between the two parts 2 and 3 of the basic body 1.

What is claimed is:

1. A lysimeter probe for insertion into the ground, comprising an elongated tubular basic body having a first end, a second end opposite said first end and an elongated interior cavity and comprising first and second sections detachably mounted to each other to form a substantially rigid structure for bearing axial compressive loads as the lysimeter probe is inserted into the ground, said first and second sections defining a substantially cylindrical recess between said first and second ends, said recess having a first selected length, handle means mounted to said basic body adjacent said first end, and a porous tubular body having a second selected length which is less than said first selected length and circumferentially mounted about said elongated tubular basic body at said recess, an interior portion of said porous tubular body being in fluid communication with said interior cavity of said tubular basic body, whereby as the lysimeter probe is inserted lengthwise into the ground axial compressive forces created by axial penetration of the ground are borne by the elongated tubular basic body and not by the porous tubular body, thereby protecting the porous tubular body from damage from the axial compressive forces.

2. A lysimeter probe as claimed in claim 1, characterized in that said second section (3) of the basic body (1) comprises a tip for penetrating into the ground.

3. A lysimeter probe as claimed in claim 2, characterized in that a portion of said second section (3) adjacent said porous tubular body (4), and a portion of said first section (2) of said basic body (1) adjacent said porous tubular body (4) have approximately the same outside diameter and that the largest outside diameter of said porous tubular body (4) is at least as small the outside diameter of said first and second sections (2, 3) of said basic body (1).

4. A lysimeter probe as claimed in claim 1, characterized in that said first and second sections (2, 3) of said basic body (1) have limit stoppers (16, 17) for maintaining a minimum axial clearance between said porous tubular body (4) and said recess defined by first and second sections (2, 3) of said basic body (1) for reproducible clamping of said porous tubular body (4).

5. A lysimeter probe as claimed in claim 4, characterized in that said porous tubular body (4) is clamped between said first and second sections (2, 3) of said basic body (1) by using sealing washers (18, 19) which are made of an elastic material.

6. A lysimeter probe as claimed in claim 1, characterized in that said first and second sections are detachably mounted to each other be means of threads (14, 15).

7. A lysimeter probe for insertion into the ground comprising, an elongated tubular basic body (1) having in interior cavity (5) extending along the length of said body, a first part (2) and a second part (3) detachably mounted to one another, and a tip formed on said second part, a porous tubular body (4) mounted to said basic body between end portions of said first and second parts, and an elongated connecting rod (13) having threaded ends (14, 15) and connecting said second part (3) of said basic body (1) to said first part (2) of said basic body (1), and wherein openings (21) are provided in said connecting rod (13) which lead said interior cavity of said basic body (1).

8. A lysimeter probe as claimed in claim 7, characterized in that a recess (20) is formed in said second part (2) of said basic body (1) for the attachment of a twisting tool and that a handle means is provided on said first part (2) of said basic body (1).

9. A lysimeter probe for insertion into the ground comprising:

a rectilinear tubular body including a tubular central piece, a connecting rod connected at one of its ends to one end of said tubular central piece, a tip connected to the other end of said connecting rod, said connecting rod being of smaller outside diameter than said tubular central piece, a porous tubular body surrounding said connecting rod and having an outside cylindrical surface approximately coextensive with an outside surface of said tubular central piece and held in position about said connecting rod by said tip, a fluid passage extending from said porous tubular body through said tubular central piece, means for drawing fluid from said porous tubular body, through said tubular central piece and out of a second end of said tubular piece opposite said one end, handle means mounted to said second end of said tubular central piece, whereby the tip of the probe is urged into the ground by applying force against the handle and the compressive forces between the tip and the handle are transmitted primarily through the connecting rod substantially without being transmitted through the porous tubular body and fluid is drawn from the porous tubular body through the fluid passage for collection above the ground surface.

* * * * *